(12) United States Patent
Tahara et al.

(10) Patent No.: US 8,095,327 B2
(45) Date of Patent: *Jan. 10, 2012

(54) POWER SUPPLY APPARATUS FOR OPERATION

(75) Inventors: Naoko Tahara, Hachioji (JP); Koh Shimizu, Kodaira (JP)

(73) Assignee: Olympus Medical Systems Corp. (JP)

( * ) Notice: Subject to any disclaimer, the term of this patent is extended or adjusted under 35 U.S.C. 154(b) by 890 days.

This patent is subject to a terminal disclaimer.

(21) Appl. No.: 12/103,049

(22) Filed: Apr. 15, 2008

(65) Prior Publication Data

US 2009/0259244 A1 Oct. 15, 2009

(51) Int. Cl.
*A61B 17/32* (2006.01)
(52) U.S. Cl. .......................................................... 702/66
(58) Field of Classification Search ..................... 702/66
See application file for complete search history.

(56) References Cited

U.S. PATENT DOCUMENTS

2002/0049551 A1  4/2002  Friedman

FOREIGN PATENT DOCUMENTS

JP  2003-159259  6/2003
JP  2005-102811  4/2005

*Primary Examiner* — Tung S Lau
(74) *Attorney, Agent, or Firm* — Ostrolenk Faber LLP (57) ABSTRACT

A power supply apparatus for operation for outputting power to a surgical instrument includes a temperature detection section for detecting a temperature of the surgical instrument, and an abnormality detection section for detecting an abnormality of the surgical instrument on the basis of the detected temperature. The temperature detection section detects the temperature by measuring the electric capacitance of the surgical instrument or directly measures the temperature of the surgical instrument by using a temperature measurement device. More specifically, the abnormality detection section detects the abnormality according to whether or not a temperature variation amount of the surgical instrument per unit time exceeds a predetermined threshold. Further, when the abnormality detection section detects an abnormality, the abnormality detection section stops the output of the power to the surgical instrument. By detecting an abnormality in the manner described above, the surgical instrument can be prevented from being broken.

7 Claims, 10 Drawing Sheets

POWER SUPPLY APPARATUS FOR OPERATION

BACKGROUND OF THE INVENTION

1. Field of the Invention

The present invention relates to a power supply apparatus for operation.

2. Description of the Related Art

A drive apparatus for an ultrasonic vibrator is hitherto known as a power supply apparatus for operation. For example, in Jpn. Pat. Appln. KOKAI Publication No. 2005-102811, a probe from which a resonant frequency is output by phase-locked loop (PLL) control is described, and in Jpn. Pat. Appln. KOKAI Publication No. 2003-159259, a method for distinguishing breakage of a defective hand-piece in an ultrasonic surgical system and breakage of a defective blade from each other is disclosed. Further, in US2002-0049551, a method for clarifying a difference between a loaded blade and a cracked blade by evaluating a measured impedance difference is disclosed.

BRIEF SUMMARY OF THE INVENTION

A first aspect of the present invention relates to a power supply apparatus for operation for outputting power to a surgical instrument, the apparatus comprising: a temperature detection section for detecting a temperature of the surgical instrument; and an abnormality detection section for detecting an abnormality of the surgical instrument on the basis of the detected temperature.

Further, a second aspect of the present invention relates to the first aspect, and the temperature detection section detects the temperature by measuring the electric capacitance of the surgical instrument or directly measures the temperature of the surgical instrument by using a temperature measurement device.

Further, a third aspect of the present invention relates to the first aspect, and the abnormality detection section detects the abnormality according to whether or not a temperature variation amount of the surgical instrument per unit time exceeds a predetermined threshold.

Further, a fourth aspect of the present invention relates to any one of the first to third aspects, and the abnormality detection section further detects the abnormality according to whether or not a variation amount of a resonant frequency of the surgical instrument per unit time exceeds a variation amount of the resonant frequency resulting from a temperature change per predetermined unit time.

Furthermore, a fifth aspect of the present invention relates to any one of the first to third aspects, and when the abnormality detection section detects an abnormality, the abnormality detection section stops the output of the power to the surgical instrument.

Moreover, a sixth aspect of the present invention relates to any one of the first to third aspects, and the surgical instrument is provided with an ultrasonic vibrator and a probe for transmitting the vibration of the ultrasonic vibrator to a distal end thereof, and the power to be output from the apparatus is ultrasonic power for driving the ultrasonic vibrator.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

(A) in FIG. 6 is a view showing a probe part in an enlarging manner.

(B) and (C) in FIG. 6 are graphs showing frequency dependence of the impedance Z, current I, and phase difference (θV−θI) which are under the PLL control observed when a crack develops in a probe in a normal state.

DETAILED DESCRIPTION OF THE INVENTION

Figure 1:
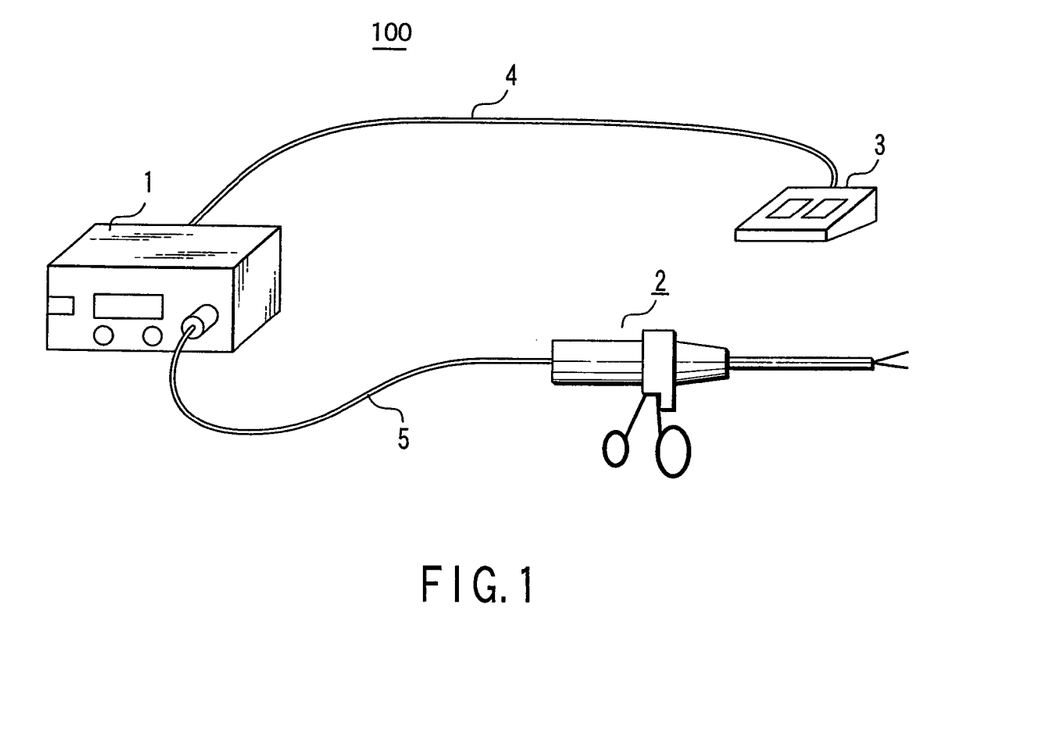
FIG. 1 is an external perspective view of an ultrasonic operation system.

Embodiments of the present invention will be described below in detail with reference to the accompanying drawings. An endoscopic surgical operation for performing medical treatment of a diseased part to be performed by using a scope for observing a state in an abdominal cavity of a patient is known. FIG. 1 is an external perspective view of an ultrasonic operation system used as an example of a system for such an endoscopic surgical operation. The ultrasonic operation system is constituted of an ultrasonic power source unit 1 serving as a power supply apparatus for operation for generating an ultrasonic output for driving an ultrasonic vibrator which is a surgical instrument, a hand-piece 2 serving as an ultrasonic surgical instrument for performing treatment by using an ultrasonic output supplied from the ultrasonic power source unit 1 through a cable 5, and a foot switch 3 connected to the ultrasonic power source unit 1 through a cable 4, for controlling the ultrasonic output from the ultrasonic power source unit 1. As the ultrasonic vibrator, for example, a bolt-clamped Langevin type transducer (BLT) is known.

Figure 2:
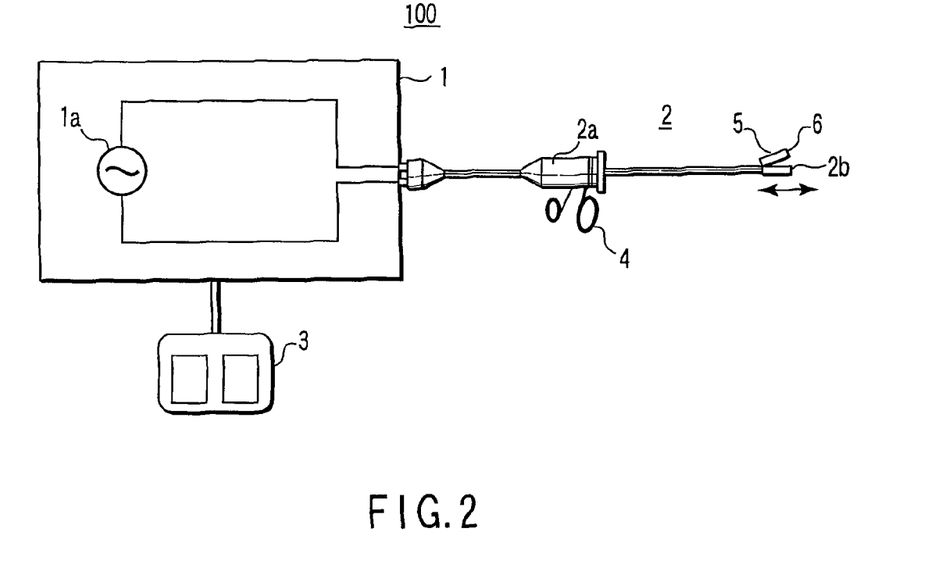
FIG. 2 is a view showing a schematic configuration of the ultrasonic operation system.

In FIG. 2, the hand-piece 2 is constituted of a hand-piece main body section 2a which includes handles 4, and in which an ultrasonic vibrator (not shown) is incorporated, and a probe 2b for transmitting vibration of the ultrasonic vibrator to a treatment section 5. The ultrasonic power source unit 1 is provided with an ultrasonic oscillator circuit 1a for generating electric energy for vibrating the ultrasonic vibrator. An electric signal output from the ultrasonic power source unit 1 is converted into mechanical vibration (ultrasonic vibration) by the ultrasonic vibrator inside the hand-piece main body section 2a, and thereafter the vibration is transmitted by the probe 2b to the treatment section 5. The treatment section 5 is provided with a grasping section 6 called a jaw driven to be opened or closed with respect to the distal end of the probe 2b. When the handles 4 are operated, the grasping section 6 is driven to be opened or closed with respect to the distal end of the probe 2b, and coagulation or incision of living tissue is performed by utilizing frictional heat generated by holding the living tissue between the distal end of the probe 2b and the grasping section 6 and applying the ultrasonic vibration thereto.

In this probe 2b, a crack is caused due to a scratch received when the probe 2b comes into contact with forceps or a clip during an operation. When a crack is caused to the probe 2b during an operation, it is necessary to immediately stop ultrasonic vibration, and replace the probe with a new one. If the operation is continued in the state where the crack is caused to the probe, it is conceivable that there is the possibility of the probe part being broken and falling off. Accordingly, it becomes necessary to detect the occurrence of the crack at an early stage, and inform the medical pursuer of the occurrence of the crack. The ultrasonic operation system will be described below in detail, and an apparatus and a method for exactly detecting an occurrence of a crack in a probe in an early stage will be described.

Figure 3:
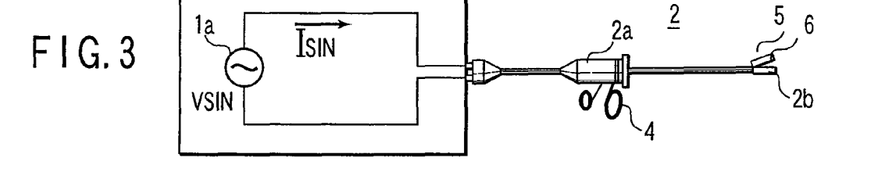
FIG. 3 is a view showing a state where a drive current generated in an ultrasonic power source unit flows to the hand-piece side.
Figure 4:
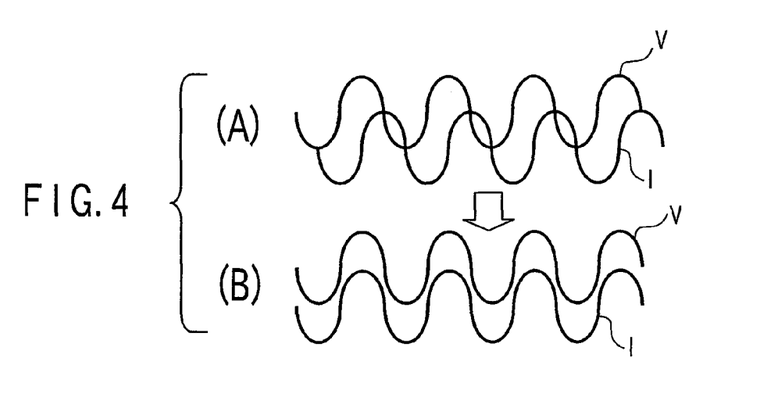
FIG. 4 is a view showing a relationship between a voltage phase and a current phase.
Figure 5:
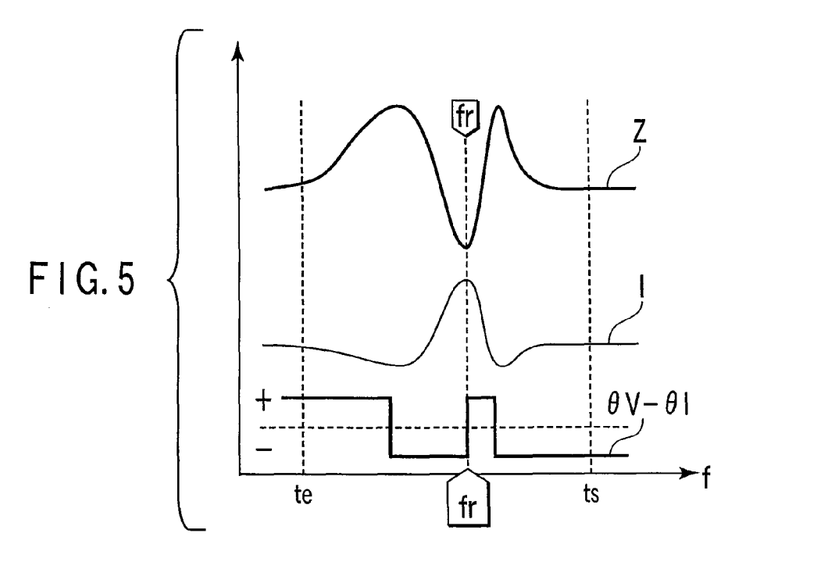
FIG. 5 is a view for explaining a procedure for scanning for a resonant frequency fr.

FIGS. 3 to 5 are views for explaining a method of controlling ultrasonic drive in an ultrasonic operation system. In FIG. 3, in an ultrasonic oscillator circuit 1a, a sinusoidal drive voltage VSIN is generated. When a sinusoidal drive current ISIN corresponding to the sinusoidal drive voltage VSIN flows into the ultrasonic vibrator inside the hand-piece main body section 2a, the ultrasonic vibrator converts the electric signal into mechanical vibration, and transmits the mechanical vibration to the distal end of the probe 2b. In the ultrasonic drive described above, when the ultrasonic vibration is output at a constant oscillation frequency, a phase difference occurs between the voltage V and the current I, and hence the drive efficiency lowers. Thus, a control circuit is provided in the ultrasonic power source unit 1, and the drive of the ultrasonic vibrator is performed while a resonance point at which a phase difference between the voltage V and the current I becomes 0 ((B) in FIG. 4) is searched for.

For example, in FIG. 5, the abscissa indicates the frequency f, and the ordinate indicates the impedance Z, current I, and phase difference ($\theta V - \theta I$). A value ($\theta V - \theta I$) indicates a phase difference. In this embodiment, a resonant frequency fr at which the phase difference ($\theta V - \theta I$) becomes 0 is detected by scanning for a point at which the impedance Z is minimized while consecutively changing the frequency. The control circuit 1c starts to perform the drive of the ultrasonic vibrator at the detected resonant frequency fr.

Figure 6:
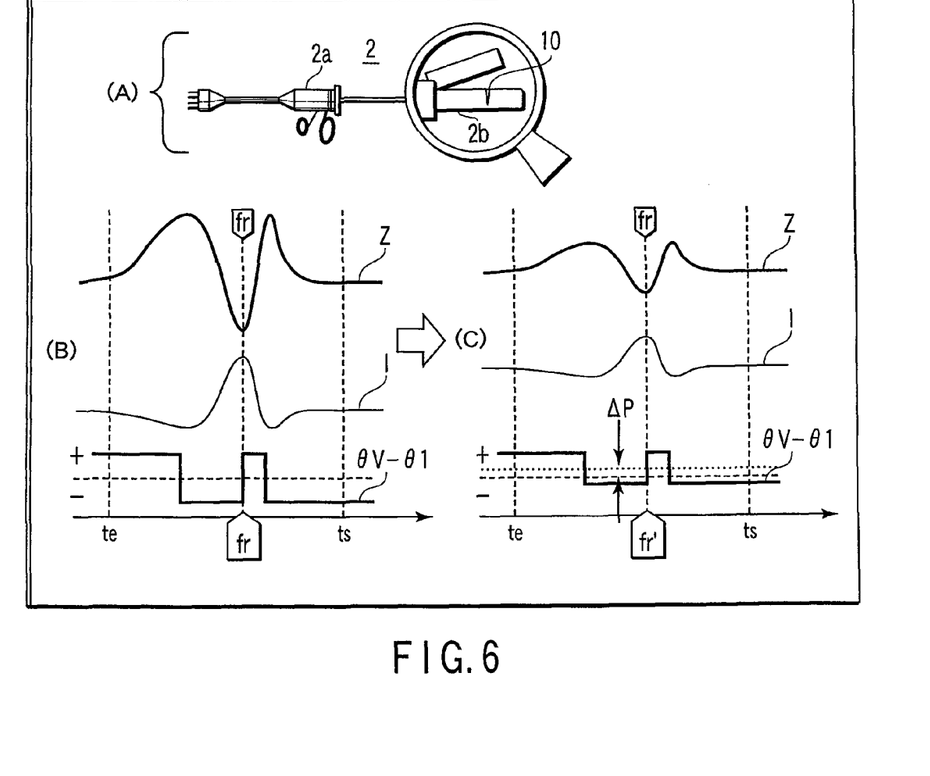

First Embodiment (A) to (B) in FIG. 6 are views for explaining a method of investigating an abnormality of a hand-piece 2 according to a first embodiment. (A) in FIG. 6 is a view showing a probe 2b part of the hand-piece 2 in an enlarging manner. This view schematically shows a state where the probe 2b has a crack 10. Here, the term crack does not necessarily imply a crack that can be confirmed with the naked eye, and includes a crack that does not appear externally, such as an internal crack, and a microcrack that appears at the early stage of metal fatigue. In the actual crack measurement, not only megascopic observation, but also microscopic observation using a magnifying glass, a metallurgical microscope or the like, and observation of a crack (microcrack) in the order of microns using an electron microscope are performed.

Measurement was conducted in detail so as to observe what variation occurs in the impedance Z and the phase difference ($\theta V - \theta I$) until a normal probe is cracked. The results are shown below.

(B) and (C) in FIG. 6 are graphs showing frequency dependence of the impedance Z, current I, and phase difference ($\theta V - \theta I$) which are under the PLL control observed when a crack has developed in the probe 2b in the normal state. At (B) in FIG. 6, the probe is not yet damaged, and the impedance Z, current I, and phase difference ($\theta V - \theta I$) which are in the normal state are shown. The frequency is varied by the PLL control such that the phase difference ($\theta V - \theta I$) becomes zero degree. At (B) in FIG. 6, the phase difference ($\theta V - \theta I$) becomes also zero degree in the vicinity of a frequency at which the impedance Z becomes the lowest. Accordingly, this frequency fr is the resonant frequency.

(C) in FIG. 6 shows a graph of the impedance Z, current I, and phase difference ($\theta V - \theta I$) under the PLL control observed after the probe 2b is cracked. When the crack develops in the probe 2b, it is conceivable that the phase difference ($\theta V - \theta I$) is shifted, and the impedance is also largely varied. Further, the PLL control is performed such that the impedance becomes the minimum, and a new resonant frequency fr' is searched for. (C) in FIG. 6 shows the impedance Z, current I, and phase difference ($\theta V - \theta I$) observed after the search, and it can be seen that the control is performed such that the phase difference ($\theta V - \theta I$) becomes in the vicinity of zero at the new resonant frequency fr'. However, it can also be seen that the minimum value of the impedance Z is larger than that at (B) in FIG. 6, and the value of the phase difference ($\theta V - \theta I$) is also at a value (dotted line) higher than the zero value (broken line) before the occurrence of the crack by $\Delta P$. In the illustration of the phase difference ($\theta V - \theta I$) shown at (B) and (C) in FIG. 6, the degree of the positive/negative magnitude, and the polarities are shown schematically and rectangularly only for easy understanding. The characters $\Delta P$ indicating the variation in the phase difference ($\theta V - \theta I$) can also be produced by factors other than the crack in the probe. However, the value is several degrees or less, and a variation exceeding 10 degrees is attributable to a crack.

Even when the PLL control is performed, the impedance Z is varied by the crack produced in the probe 2b. Particularly, an electric capacitance component of the impedance is increased. It was found that this electric capacitance component was increased due to the temperature rise of the ultrasonic vibrator serving as a surgical instrument.

The reason why the temperature of the ultrasonic vibrator is raised can be conceivable that the probe 2b cannot sufficiently exhibit the function of the probe serving as a complete vibration transmitting element of the ultrasonic vibrator due to the crack, and another unintended vibration mode resulting from the crack has occurred. Another unintended vibration mode is superposed on the normal vibration mode, or interferes the normal vibration mode. Further, the normal vibration mode and another unintended vibration mode interfere with each other, and a large periodic vibration mode is caused in some cases. It is conceivable that heat is abnormally generated in the ultrasonic vibrator by these vibration modes, and the increase in the electric capacitance is caused by the generation of heat.

Figure 7:
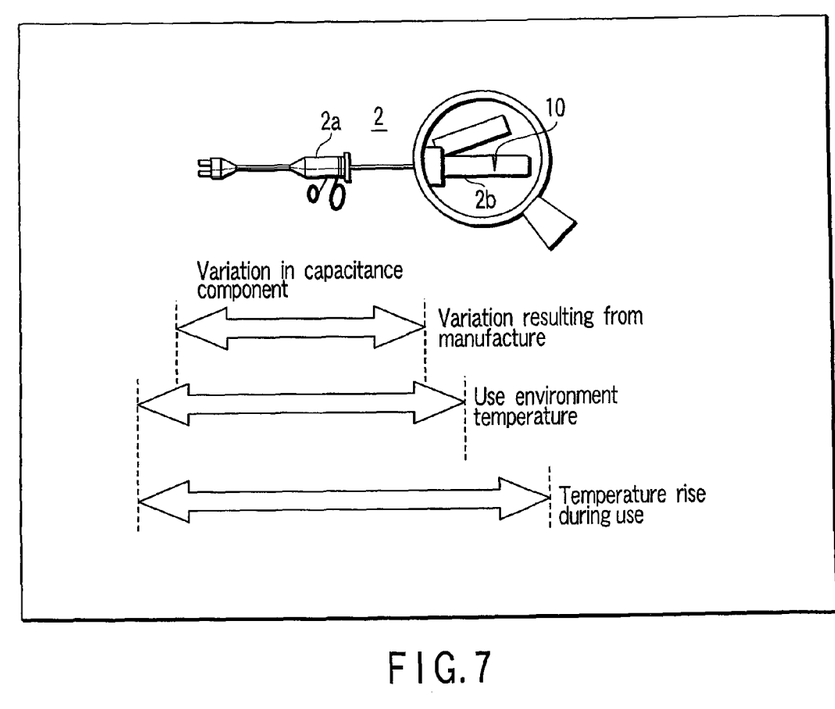
FIG. 7 is a schematic view for explaining a first embodiment, and showing magnitude of each factor in the causation of a variation in a capacitance component.

FIG. 7 shows the magnitude of each factor in the causation of a variation in the electric capacitance by the size of the arrow. As for the factors in the causation of the variation in the capacitance component, the variation in the product resulting from the manufacture, use environment temperature, and temperature rise during use which become larger in the order mentioned are present. From the above fact, when the unintended vibration mode is caused by the crack 10 of the probe 2b, the temperature is further more raised as compared with the temperature rise in the normal use. Thus, it can be understood that the variation in the capacitance component resulting from the above is the largest. The temperature rise during normal use differs depending on the type of the ultrasonic vibrator. In a certain type of ultrasonic vibrator, a temperature rise of a maximum of 10° C. is observed during use, and in another type of ultrasonic vibrator, a temperature rise of a maximum of 30° C. is observed. By the temperature rise of these ultrasonic vibrators, a variation in the electric capacitance of about 72 to 180 pF is observed. The correlation between the temperature rise of the ultrasonic vibrator and the variation in the resonant frequency can be measured in advance. Further, it is also known that the temperature of the ultrasonic vibrator is well correlated with the electric capacitance of the ultrasonic vibrator. Accordingly, the tempaerature of the ultrasonic vibrator can be obtained with high accuracy by measuring, for example, the electric capacitance of the ultrasonic vibrator, and the variation amount of the resonant frequency can also be estimated on the basis of the temperature.

As described above, the electric capacitance is changed by the abnormal heat generation of the ultrasonic vibrator, and the impedance including the electric capacitance is also changed. It is conceivable that as a result of this, the frequency characteristic of the impedance is changed, and the frequency dependence of the phase difference ($\theta V - \theta I$) between the voltage and the current is also changed. On the basis of these results, it is possible to measure that a crack 10 has been produced in the probe 2b by monitoring the temperature of the ultrasonic vibrator under the PLL control or by monitoring the temperature of the hand-piece 2 including the ultrasonic vibrator.

Further, it is also possible to directly measure the temperature of the ultrasonic vibrator of the hand-piece 2 by means of a thermistor or a thermocouple which is a temperature measurement device. The temperature measurement to be mentioned hereafter implies both the temperature measurement in which calculation is based on the electric capacitance measurement, and the measurement performed by directly using a thermistor or a thermocouple.

Figure 8:
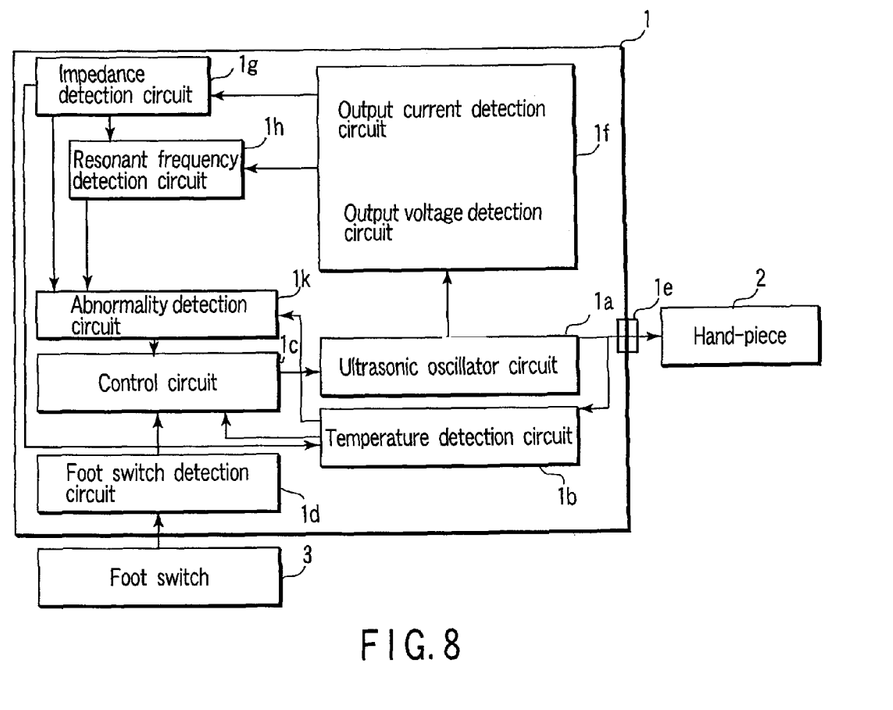
FIG. 8 is a functional block diagram for explaining a function of each unit in an ultrasonic power source unit in an ultrasonic operation system.

FIG. 8 is a functional block diagram for explaining a function of each unit in an ultrasonic power source unit in an ultrasonic operation system. The hand-piece 2 is connected to the ultrasonic power source unit 1 through a connector 1e. In the ultrasonic power source unit 1, an ultrasonic oscillator circuit 1a, output voltage/output current detection circuit 1f, impedance detection circuit 1g, resonant frequency detection circuit 1h, temperature detection circuit 1b, foot switch detection circuit 1d, and control circuit 1c are provided. The ultrasonic oscillator circuit 1a is a part for generating a drive signal for driving the ultrasonic vibrator inside the hand-piece 2. The foot switch detection circuit 1d is a part for detecting that the foot switch 3 has been operated by the operator.

When the foot switch 3 is operated by the operator, the operation signal is transmitted to the control circuit 1c through the foot switch detection circuit 1d. The control circuit 1c performs control such that the ultrasonic power is output from the ultrasonic oscillator circuit 1a to the hand-piece 2.

The output voltage/output current detection circuit 1f is a part for detecting an output voltage and an output current of the power supplied from the ultrasonic oscillator circuit 1a to the ultrasonic vibrator. The values of the output voltage and the output current detected by the output voltage/output current detection circuit 1f are input to the impedance detection circuit 1g and the resonant frequency detection circuit 1h. The impedance detection circuit 1g detects the impedance by using the impedance detection algorithm of the hand-piece 2 on the basis of the values of the input output voltage and the input output current, and the phase difference between them. The impedance measured here can be separated into an electric capacitance component and an electric conductance component. In the temperature measurement to be described later, the temperature can be calculated by using the electric capacitance component.

The resonant frequency detection circuit 1h detects a frequency actually applied to the probe 2b from the output voltage and the output current detected by the output voltage/output current detection circuit 1f, and at the same time, monitors a variation in the impedance value transmitted from the impedance detection circuit 1g. A frequency at which the value of the impedance abruptly changes is obtained, and detected as the resonant frequency.

The temperature detection circuit 1b may calculate the temperature from the electric capacitance measurement of the hand-piece 2, or may directly measure the temperature by using a thermistor or a thermocouple provided in the hand-piece 2. The impedance detection circuit 1g transmits the measured electric capacitance to the temperature detection circuit 1b, and the temperature detection circuit 1b can calculate the temperature from the electric capacitance transmitted thereto on the basis of a correlation between the temperature measured in advance and the electric capacitance. Further, as the method for directly measuring the temperature, a signal detected by, for example, a thermistor or a thermocouple may be introduced into the temperature detection circuit 1b, and the temperature measurement may be performed chronologically. The temperature measured by the temperature detection circuit 1b is stored in the internal storage part. More specifically, the value of the temperature is saved in a memory which is the storage part at intervals of, for example, 5 msec, and the consecutively measured value of the temperature and the previously saved value of the temperature are compared with each other. Further, the value of the temperature measured at intervals of 5 msec is compared with plural values of the temperature such as values measured 5 msec ago, 10 msec ago, 15 msec ago, and so on, thereby judging whether or not the variation in the value of the temperature is not abnormal.

Figure 9:
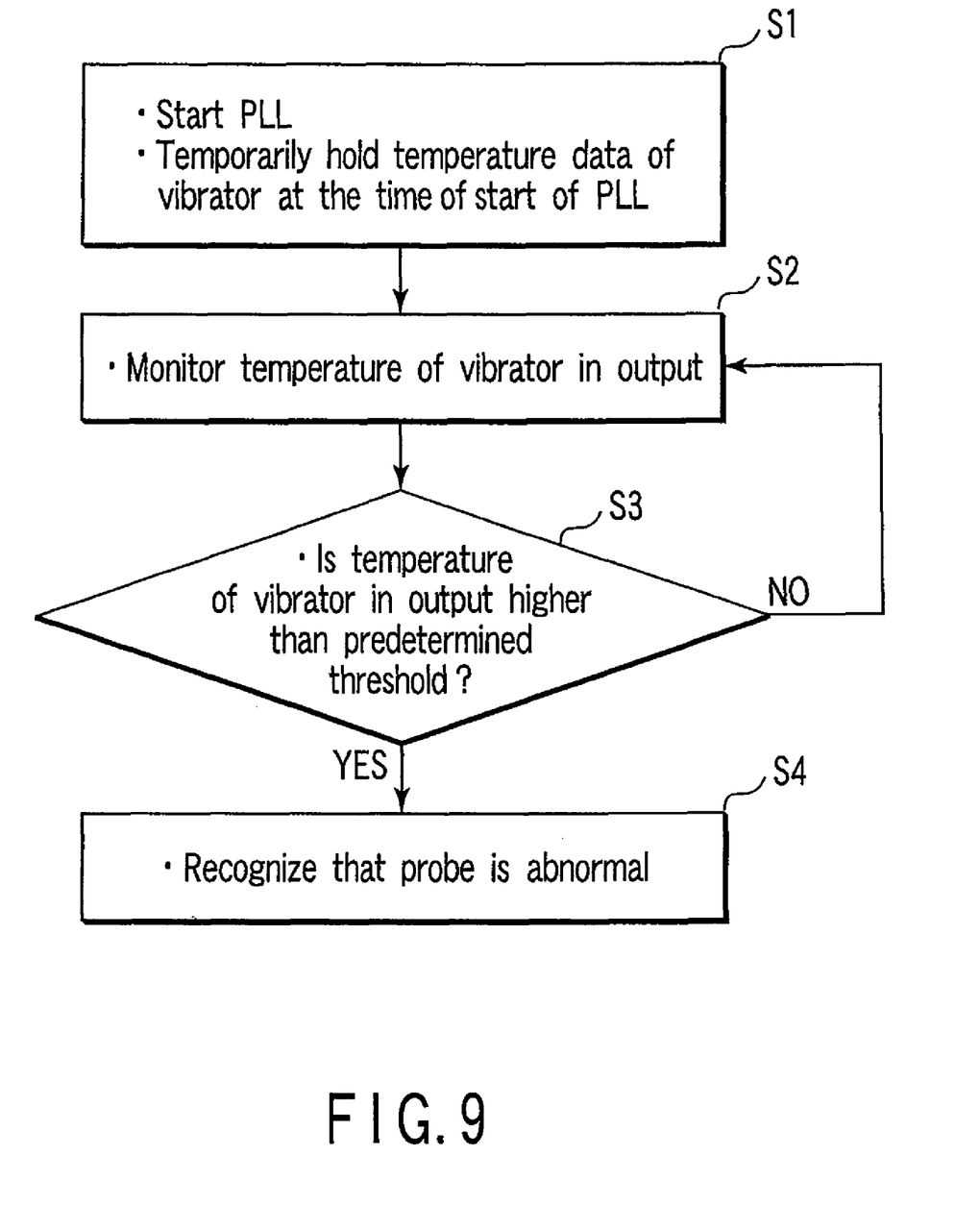
FIG. 9 is a flowchart for detecting an abnormality of a probe according to a first embodiment.

The above flow will be described below by using the block diagram of FIG. 8 and the flowchart of FIG. 9. First, when an operation in an abdominal cavity of a patient is performed by using an ultrasonic probe 2b, the control circuit 1c starts the PLL control, and the abnormality detection circuit 1k detects the initial temperature of the ultrasonic vibrator, and stores the detected data (step S1). The PLL control is the control necessary for the ultrasonic probe to perform an operation with increased energy efficiency. While the ultrasonic power is output from the ultrasonic oscillator circuit 1a to the hand-piece 2, the abnormality detection circuit 1k monitors the variation in the temperature at intervals of a fixed sampling time determined in advance (step S2). The monitored temperature is compared with a plurality of resonant frequency data items detected previously. For example, the abnormality detection circuit $1k$ determines to set the sampling time at 5 msec, and compares each of 20 samples of the temperature (temperature measurement values within a period of 5 msec× 20 samples=100 msec) detected previously, or an average value of the 20 samples of the temperature detected previously with a currently detected temperature. The abnormality detection circuit $1k$ compares the temperature with a predetermined threshold, for example, 30° C. (step S3), and judges that the probe is abnormal when the temperature value is larger than the threshold (step S4). When the temperature value is smaller than the threshold, the abnormality detection circuit $1k$ judges that the probe $2b$ is normal, and returns to step S2 to continue monitoring the variation in the temperature.

A correlation between the actually measured value of the temperature and the crack occurrence status of the probe $2b$ was measured. As a result of the measurement, when the variation in the temperature exceeds 30° C., a crack that can be visually confirmed, or a microcrack that can be confirmed by using an electron microscope occurred.

Further, when the probe is judged to be abnormal, it is possible to stop or shut down the ultrasonic output, and prevent breakage or falling off of the probe greater than the crack.

(Effect)

According to this embodiment, the temperature is detected on the basis of the measurement of the electric capacitance or on the basis of direct measurement, the variation value of the temperature is monitored, and a temperature variation value different from a temperature variation value resulting from resection or the like of living tissue by an ordinary operation is detected as an abnormality, whereby it is possible to instantaneously and easily grasp an occurrence of a crack in the probe. By virtue of the detection of the probe crack in the early stage, the medical staff can replace the probe before the breakage of the probe occurs, and safely continue the treatment of the patient.

Second Embodiment

Figure 10:
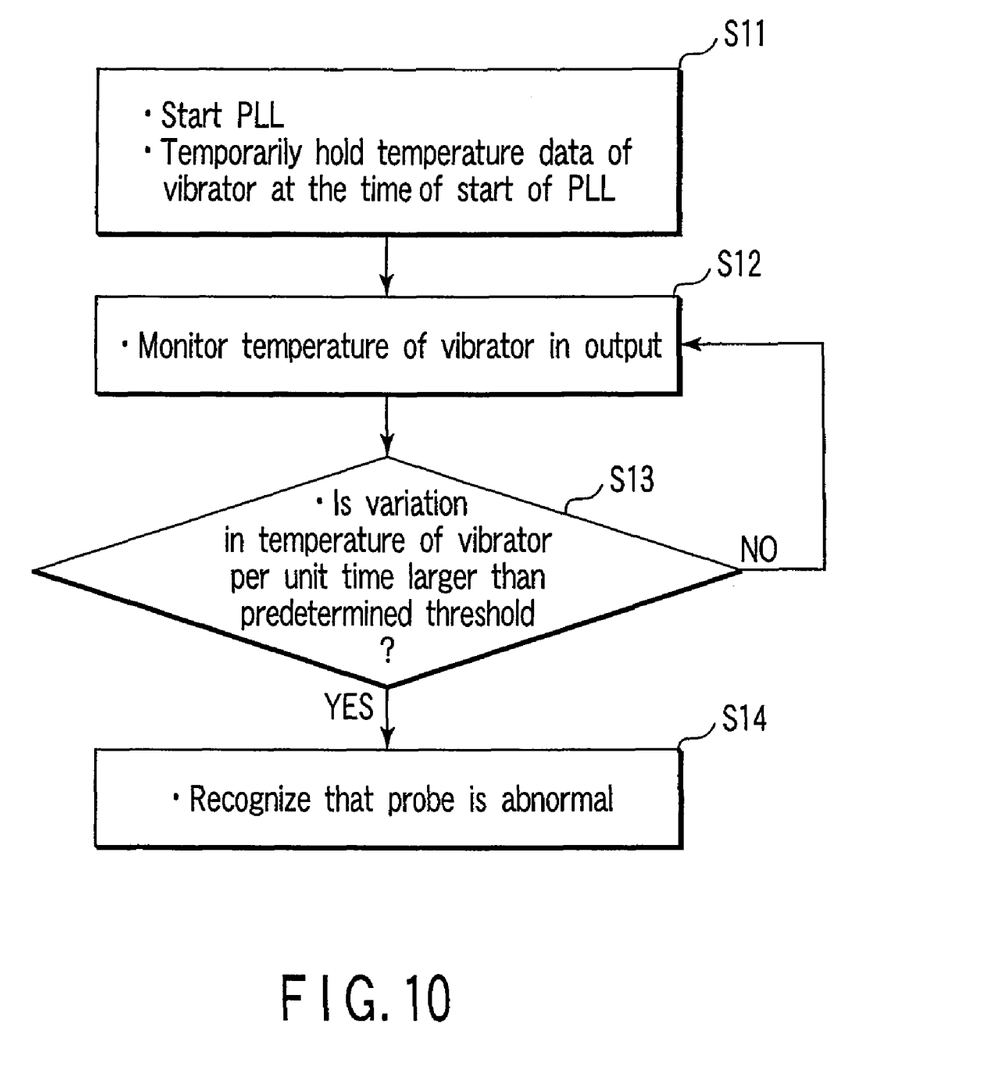
FIG. 10 is a flowchart for detecting an abnormality of a probe according to a second embodiment.

A second embodiment of the present invention will be described below by using the flowchart of FIG. 10. Here, only parts different from the first embodiment will be described. Steps S1 and S2 in the flowchart of FIG. 9 correspond to steps S11 and S12 in the flowchart of FIG. 10, and hence a detailed description will be omitted.

The temperature monitored in step S12 is compared with a plurality of temperature data items detected previously. For example, an abnormality detection circuit $1k$ compares a variation in the temperature per unit time (100 msec) with a predetermined threshold, for example, 1° C./100 msec (step S13), and when the variation is larger than the threshold, the abnormality detection circuit $1k$ judges that the probe is abnormal (step S14). When the variation is smaller than the threshold, the abnormality detection circuit $1k$ judges that the probe is normal, and returns to step S12 to continue monitoring the variation in the temperature.

A correlation between the actually measured value of the temperature and the crack occurrence status of the probe $2b$ was measured. As a result of the measurement, when the variation in the temperature per unit time exceeds 5° C./100 msec, a crack that can be visually confirmed, or a microcrack that can be confirmed by using an electron microscope occurred.

Further, when the probe is judged to be abnormal, it is possible to stop or shut down the ultrasonic output, and prevent breakage or falling off of the probe greater than the crack.

(Effect)

According to this embodiment, the temperature is detected, the temperature variation value of the temperature per unit time is monitored, and a temperature variation value different from a temperature variation value resulting from resection or the like of living tissue by an ordinary operation is detected as an abnormality, whereby it is possible to instantaneously and easily grasp an occurrence of a crack in the probe. By virtue of the detection of the probe crack in the early stage, the medical staff can replace the probe before the breakage of the probe occurs, and safely continue the treatment of the patient.

Third Embodiment

Figure 11:
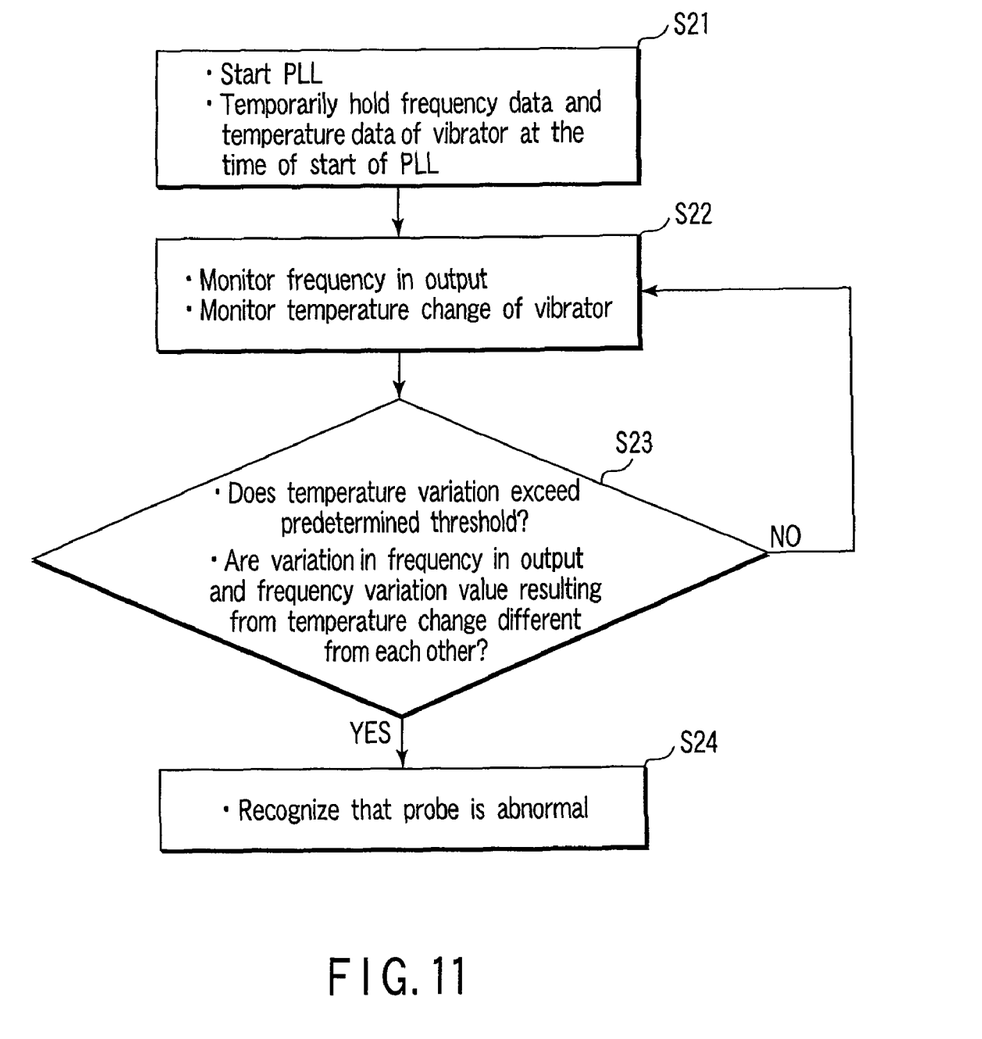
FIG. 11 is a flowchart for detecting an abnormality of a probe according to a third embodiment.

A third embodiment of the present invention will be described below by using the block diagram of FIG. 8 and the flowchart of FIG. 11. First, when an operation in an abdominal cavity of a patient is performed by using an ultrasonic probe $2b$, a control circuit $1c$ starts the PLL control, and an abnormality detection circuit $1k$ detects the initial resonant frequency and the initial temperature of the ultrasonic vibrator, and stores the detected data items (step S21). While the ultrasonic power is output from an ultrasonic oscillator circuit $1a$ to a hand-piece 2, the abnormality detection circuit $1k$ monitors the variation in the resonant frequency and the temperature at intervals of a fixed sampling time determined in advance (step S22). The monitored resonant frequency and the temperature are compared with a plurality of resonant frequency data items and a plurality of temperature data items detected previously. For example, the abnormality detection circuit $1k$ determines to set the sampling time at 5 msec, and compares each of 20 samples of the resonant frequency and the temperature (frequency measurement values and temperature measurement values within a period of 5 msec×20 samples=100 msec) detected previously, or average values of the 20 samples of the resonant frequency and the temperature detected previously with a currently detected resonant frequency and temperature. More specifically, the abnormality detection circuit $1k$ compares the temperature with a predetermined threshold, for example, 30° C. The abnormality detection circuit $1k$ compares the variation amount of the temperature with the predetermined threshold, and compares the variation amount of the resonant frequency with a variation amount of the resonant frequency caused by a temperature change that can be expected when a treatment such as an operation is performed. When the variation amount exceeds the expected variation amount, the abnormality detection circuit $1k$ judges that the probe is abnormal (step S23). As described above, by also using the variation amount of the resonant frequency for the judgment of the abnormality in parallel with the temperature, an abnormality judgment can be made with higher accuracy.

A correlation between the actually measured value of the temperature and the crack occurrence status of the probe $2b$ was measured. As a result of the measurement, when the variation in the temperature exceeds 30° C., and the variation amount of the resonant frequency also exceeds the predetermined variation amount, a crack that can be visually confirmed, or a microcrack that can be confirmed by using an electron microscope occurred.

(Effect)

It is effective to set a variation in the resonant frequency resulting from the temperature of the ultrasonic vibrator as a predetermined threshold with respect to the variation amount of the resonant frequency per unit time together with a variation amount of the temperature. By this setting method of the threshold, it is possible to accurately and easily distinguish a change in the resonant frequency resulting from the temperature rise at the time of an ordinary operation and a change in the resonant frequency resulting from a crack of the probe 2b from each other. In accordance with the above, it is possible to stop or shut down the ultrasonic output, and prevent breakage or falling off of the probe greater than the crack.

Fourth Embodiment

Figure 12:
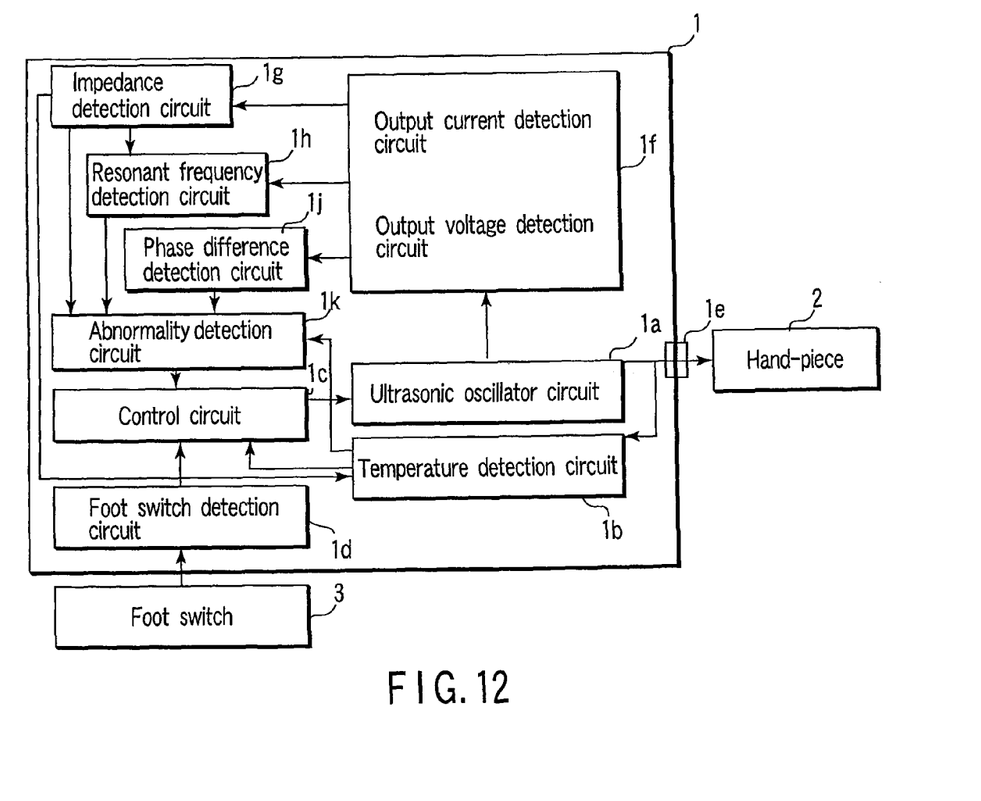
FIG. 12 is a functional block diagram for explaining a function of each unit in an ultrasonic power source unit in an ultrasonic operation system according to a fourth embodiment.

A fourth embodiment will be described below with reference to the block diagram of FIG. 12. This block diagram resembles the block diagram of FIG. 8, and includes a phase difference detection circuit 1j in addition to the block diagram of FIG. 8. It is known that a phase difference ($\theta V-\theta I$) between an output voltage and an output current detected by the phase difference detection circuit 1j is varied by a crack of the probe 2b from (B) and (C) in FIG. 6. The variation in the phase difference can be further used as the abnormality judgment means. Further, the abnormality detection circuit 1k acquires signals of the output voltage and the output current from an output voltage/output current detection circuit 1f. It is known that the output current or the like is also varied by the crack of the probe 2b from (B) and (C) in FIG. 6. Accordingly, the variation in the output current or the like can further be used as the abnormality judgment means.

(Effect)

By measuring a variation amount of the phase difference ($\theta V-\theta I$) or the output current or the like, a crack of the probe can be grasped more accurately and appropriately.

What is claimed is:

1. A power supply apparatus for operation for outputting power to a surgical instrument comprising:

a temperature detection section for directly detecting a temperature of the surgical instrument by a temperature measurement device provided at the surgical instrument; and an abnormality detection section for detecting an abnormality of the surgical instrument on the basis of the detected temperature.

2. The power supply apparatus for operation according to claim 1, wherein the abnormality detection section detects the abnormality according to whether or not a temperature variation amount of the surgical instrument per unit time exceeds a predetermined threshold.

3. The power supply apparatus for operation according to any one of claims 1 to 2, wherein the abnormality detection section further detects the abnormality according to whether or not a variation amount of a resonant frequency of the surgical instrument per unit time exceeds a variation amount of the resonant frequency resulting from a temperature change per predetermined unit time.

4. The power supply apparatus for operation according to any one of claims 1 to 2, wherein when the abnormality detection section detects an abnormality, the abnormality detection section stops the output of the power to the surgical instrument.

5. The power supply apparatus for operation according to any one of claims 1 to 2, wherein the surgical instrument is provided with an ultrasonic vibrator and a probe for transmitting the vibration of the ultrasonic vibrator to a distal end thereof, and the power to be output from the apparatus is ultrasonic power for driving the ultrasonic vibrator.

6. The power supply apparatus according to claim 1, wherein the temperature measurement device comprises a thermistor.

7. The power supply apparatus according to claim 1, wherein the temperature measurement device comprises a thermocouple.

* * * * *